US009782066B2

(12) United States Patent
Utagawa et al.

(10) Patent No.: US 9,782,066 B2
(45) Date of Patent: Oct. 10, 2017

(54) IMAGING APPARATUS AND CONTROL METHOD FOR THE SAME

(71) Applicant: CANON KABUSHIKI KAISHA, Tokyo (JP)

(72) Inventors: Tsutomu Utagawa, Yokohama (JP); Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/040,073

(22) Filed: Feb. 10, 2016

(65) Prior Publication Data

US 2016/0235294 A1   Aug. 18, 2016

(30) Foreign Application Priority Data

Feb. 17, 2015   (JP) ................................ 2015-028532

(51) Int. Cl.
| | | |
|---|---|---|
| *A61B 3/14* | (2006.01) | |
| *A61B 3/00* | (2006.01) | |
| *A61B 3/10* | (2006.01) | |
| *G02B 21/00* | (2006.01) | |

(52) U.S. Cl.
CPC .......... *A61B 3/1025* (2013.01); *A61B 3/0025* (2013.01); *G02B 21/0028* (2013.01)

(58) Field of Classification Search
USPC ................................................ 351/200–246
See application file for complete search history.

(56) References Cited

U.S. PATENT DOCUMENTS

| 6,937,255 B2 * | 8/2005 | Fukuda ................. H04N 5/265 345/633 |
|---|---|---|
| 2004/0183926 A1 | 9/2004 | Fukuda et al. |
| 2009/0086164 A1 | 4/2009 | Akita et al. |
| 2010/0220289 A1 * | 9/2010 | Hearn ................. A61B 3/1025 351/208 |

(Continued)

FOREIGN PATENT DOCUMENTS

| CN | 102525405 A | 7/2012 |
|---|---|---|
| JP | 2009-095632 A | 5/2009 |
| WO | 2016-009603 A1 | 1/2016 |

OTHER PUBLICATIONS

Extended European search report issued in corresponding application No. 16154424.2 on Jun. 20, 2016.

(Continued)

*Primary Examiner* — Mohammed Hasan
(74) *Attorney, Agent, or Firm* — Carter, DeLuca, Farrell & Schmidt, LLP

(57) ABSTRACT

Provided is an imaging apparatus capable of imaging a confocal image and a nonconfocal image, in which an image intended by an examiner is provided easily and rapidly. The imaging apparatus includes: an acquiring unit configured to acquire a confocal image and a nonconfocal image of an eye to be inspected; a display unit configured to display at least one of the acquired confocal image and the acquired nonconfocal image; an analysis unit configured to analyze the acquired confocal image and the acquired nonconfocal image; and a display control unit configured to change a display form displayed on the display unit in accordance with an analysis result obtained by the analysis unit.

9 Claims, 8 Drawing Sheets

(56) References Cited

U.S. PATENT DOCUMENTS

2012/0134563 A1* 5/2012 Nakano ................ G06T 7/0012
   382/131
2014/0185889 A1   7/2014 Yonezawa

OTHER PUBLICATIONS

U.S. Appl. No. 15/063,998, filed Mar. 8, 2016, inventor Utagawa et al.
Sulai et al., "Visualization of retinal vascular structure and perfusion with a nonconfocal adaptive optics scanning light ophthalmoscope", J. Opt. Soc. Am. A, vol. 31, No. 3, pp. 569-579, 2014.
Scoles et al., "In Vivo Imaging of Human Cone Photoreceptor Inner Segments", IOVS, vol. 55, No. 7, pp. 4244-4251, 2014.
Chinese office action issued in corresponding application No. 201610087518.2 dated Aug. 3, 2017.

* cited by examiner

IMAGING APPARATUS AND CONTROL METHOD FOR THE SAME

BACKGROUND OF THE INVENTION

Field of the Invention

The present invention relates to an imaging apparatus and a control method for the imaging apparatus, and more particularly, to an imaging apparatus to be used for ophthalmic diagnosis and treatment or the like and a control method for the imaging apparatus.

Description of the Related Art

The inspection of an eye portion has been widely conducted for the purpose of diagnosing and treating lifestyle-related diseases and diseases that are leading causes of blindness in early stages. As one of inspection apparatus for an eye portion, a scanning laser ophthalmoscope (SLO) that is an ophthalmic apparatus using a principle of a confocal laser microscope has been known. The SLO is an apparatus configured to perform raster scanning on a fundus of the eye with laser light which is measuring light and acquire a planar image of the fundus of the eye based on the intensity of return light of the measuring light with high resolution at high speed. Through the detection of only light having passed through a pinhole, the SLO can image only return light at a particular depth position to acquire an image with a high contrast compared to that of a fundus camera and the like.

Such an apparatus configured to acquire a planar image is hereinafter referred to as SLO apparatus, and the planar image is hereinafter referred to as SLO image.

In the SLO apparatus, it has become possible to acquire an SLO image of a retina with improved lateral resolution by increasing a beam diameter of measuring light. However, along with the increase in the beam diameter of the measuring light, there occurs a problem of decreases in an S/N ratio and the resolution of an SLO image of a retina due to an aberration of an eye to be inspected when the SLO image is acquired.

In order to solve the problem, there is developed an adaptive optics SLO apparatus including an adaptive optics system, in which an aberration of an eye to be inspected is measured by a wavefront sensor in real time, and aberrations of measuring light and return light thereof generated in the eye to be inspected are compensated by a wavefront compensation device. With such an adaptive optics SLO apparatus, it is possible to acquire an SLO image with high lateral resolution.

Further, the SLO image with high lateral resolution can be acquired as a moving image, and enables, for example, hemodynamics to be observed non-invasively. Therefore, through extraction of a retinal vessel from each frame, the moving speed of blood corpuscles in a capillary vessel and the like are measured. Photoreceptor cells can also be observed, and in this case, a focus position is set to the vicinity of retina outer layers, to thereby acquire an SLO image.

However, in a confocal image obtained by acquiring retina inner layers, a noise signal is strong owing to the influence of light reflecting from a nerve fiber layer, and hence it is difficult to observe a blood vessel wall and detect a wall boundary in some cases. In view of the foregoing, in recent years, a method involving obtaining scattering light by changing the diameter, shape, and position of a pinhole arranged in front of a photo-receiving unit and observing a nonconfocal image thus obtained has come to be used (Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014). In the nonconfocal image, a focus depth is large, and hence an object having irregularities in a depth direction, such as a blood vessel, can be observed easily. Further, light reflected from the nerve fiber layer is not easily received directly, and hence noise can be reduced.

Further, the following has been found. Even in the case where photoreceptor cells in the retina outer layers are observed, hitherto, a photoreceptor outer segment is mainly imaged in the confocal image, whereas irregularities of a photoreceptor inner segment are imaged in the nonconfocal image (Scoles, Dubra et al.; "In Vivo Imaging of Human Cone Photoreceptor Inner Segments", IOVS, Vol. 55, No. 7, pp. 4244-4251, 2014). Cells, in which the photoreceptor outer segment is lost but the photoreceptor inner segment exists in an initial stage of a photoreceptor cell disorder, are observed as follows: the cells can be observed to be lost in black in the confocal image, whereas the cells can be observed as a region with high brightness in the nonconfocal image.

As described above, in "Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014", there is a disclosure of a technology of acquiring a nonconfocal image of a retinal vessel through use of an adaptive optics SLO apparatus. Further, in "Scoles, Dubra et al.; "In Vivo Imaging of Human Cone Photoreceptor Inner Segments", IOVS, Vol. 55, No. 7, pp. 4244-4251, 2014, there is a disclosure of a technology of concurrently acquiring a confocal image and a nonconfocal image through use of an adaptive optics SLO apparatus.

In the SLO apparatus capable of acquiring both a confocal image and a nonconfocal image, the signal intensity of a confocal signal is much larger. Therefore, in the case of displaying an acquired fundus image, the confocal image is generally displayed. However, in the case of observing a photoreceptor cell density and the like, the state of the photoreceptor cells can be observed more correctly by using the nonconfocal image in some cases. Therefore, in an apparatus configured to acquire both a confocal image and a nonconfocal image, it is necessary to appropriately switch between the confocal image and the nonconfocal image in consideration of information intended to be acquired by an examiner. However, it is necessary to select an intended image by comparing those images, which is cumbersome in actual inspection.

SUMMARY OF THE INVENTION

The present invention has been made in view of the above-mentioned circumstances, and the present invention is to provide an imaging apparatus configured to provide an image intended by an examiner easily and rapidly by properly switching between a confocal image and a nonconfocal image in displaying an acquired image of a subject, and a control method for the imaging apparatus.

In order to solve the above-mentioned problem, according to one embodiment of the present invention, there is provided an imaging apparatus, including:
  an acquiring unit configured to acquire a confocal image and a nonconfocal image of an eye to be inspected;
  a display unit configured to display at least one of the acquired confocal image and the acquired nonconfocal image;

an analysis unit configured to analyze the acquired confocal image and the acquired nonconfocal image; and a display control unit configured to change a display form displayed on the display unit in accordance with an analysis result obtained by the analysis unit.

According to the one embodiment of the present invention, an image intended by an examiner may be provided by changing the display form, for example, switching between the confocal image and the nonconfocal image as necessary, in displaying an acquired fundus image of a subject.

Further features of the present invention will become apparent from the following description of exemplary embodiments with reference to the attached drawings.

BRIEF DESCRIPTION OF THE DRAWINGS

FIGS. 1A and 1B are each a schematic diagram for illustrating an entire configuration of an SLO apparatus according to an embodiment of the present invention, in which FIG. 1A is a plan view of the SLO apparatus, and FIG. 1B is a side view thereof.

DESCRIPTION OF THE EMBODIMENTS

Modes for carrying out the present invention are now described with reference to the drawings by way of the following embodiments. Note that, the embodiments described below do not restrict the present invention as set forth in the appended claims, and not all of the combinations of the features described in the embodiments are essential to the solution of the present invention.

First Embodiment

In a first embodiment of the present invention, an adaptive optics scanning laser ophthalmoscope (AO-SLO) apparatus to which the present invention is applied is described as an optical image acquiring apparatus. The AO-SLO apparatus includes an adaptive optics system, and is an apparatus configured to acquire a planar image (AO-SLO image) of a fundus of an eye having high lateral resolution. In addition, for the purpose of aiding acquisition of the AO-SLO image, a wide field scanning laser ophthalmoscope (WF-SLO) apparatus configured to acquire a planar image having a wide field angle (WF-SLO image), an anterior ocular segment observation device configured to grasp an incident position of measuring light, and a fixation target display device configured to guide a line of sight so as to adjust an acquiring position are associated.

In this embodiment, the AO-SLO apparatus is configured to acquire a planar image by compensating an optical aberration of an eye to be inspected by using a spatial light modulator. With the AO-SLO apparatus, a good planar image can be acquired regardless of a diopter scale and the optical aberration of the eye to be inspected.

Note that, in this embodiment, in order to acquire a planar image having high lateral resolution, the apparatus includes the adaptive optics system. However, the adaptive optics system may not be included as long as the configuration of the optical system can realize high resolution.

<Entire Configuration of Apparatus>

Figure 1A:
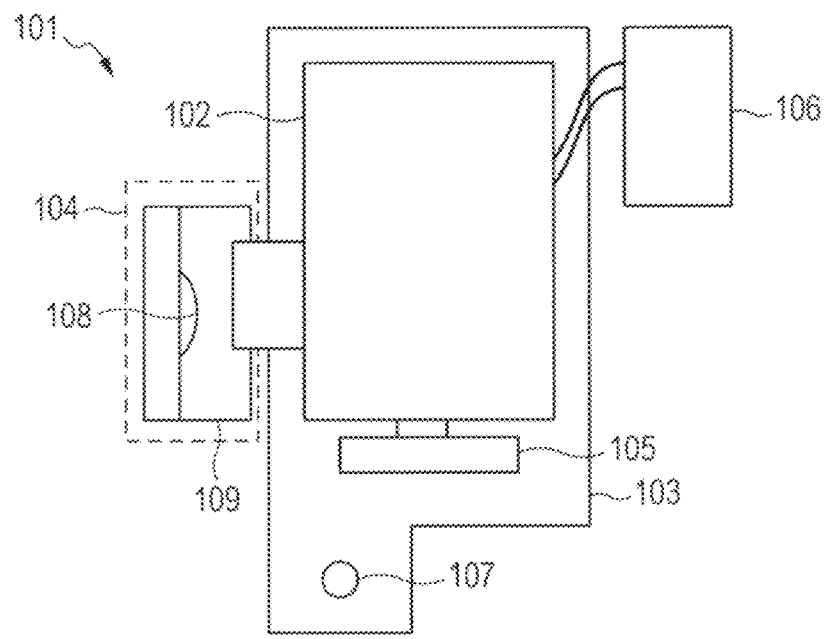
Figure 1B:
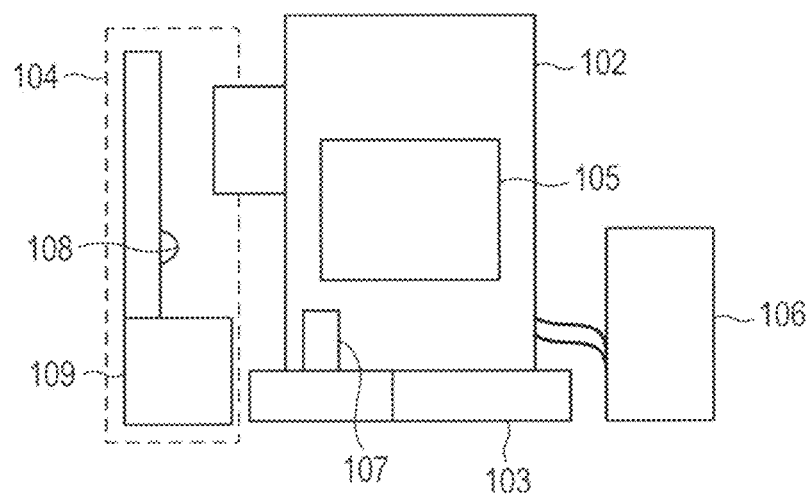

First, a schematic configuration of an AO-SLO apparatus 101 according to this embodiment is described specifically with reference to FIG. 1A and FIG. 1B.

The AO-SLO apparatus 101 roughly includes a head unit 102, a stage unit 103, a face receiving unit 104, a display unit 105, and a control unit 106. A main optical system in the AO-SLO apparatus 101 is built in the head unit 102. The stage unit 103 moves the head unit 102 in horizontal and vertical directions. The face receiving unit 104 adjusts a position for putting a face of a subject. The display unit 105 is formed of a liquid crystal monitor in this embodiment and displays an operation screen. The control unit 106 formed of a personal computer (PC) controls the entire AO-SLO apparatus 101.

The head unit 102 is installed on the stage unit 103 and can be moved in a horizontal direction by tilting a joystick 107 arranged similarly on the stage unit 103 and in a vertical direction by rotating the joystick 107. The face receiving unit 104 includes a chin holder 108 configured to receive a chin and a chin holder drive unit 109 configured to move the chin holder 108 with an electric stage.

<Configuration of Optical System>

Figure 2A:
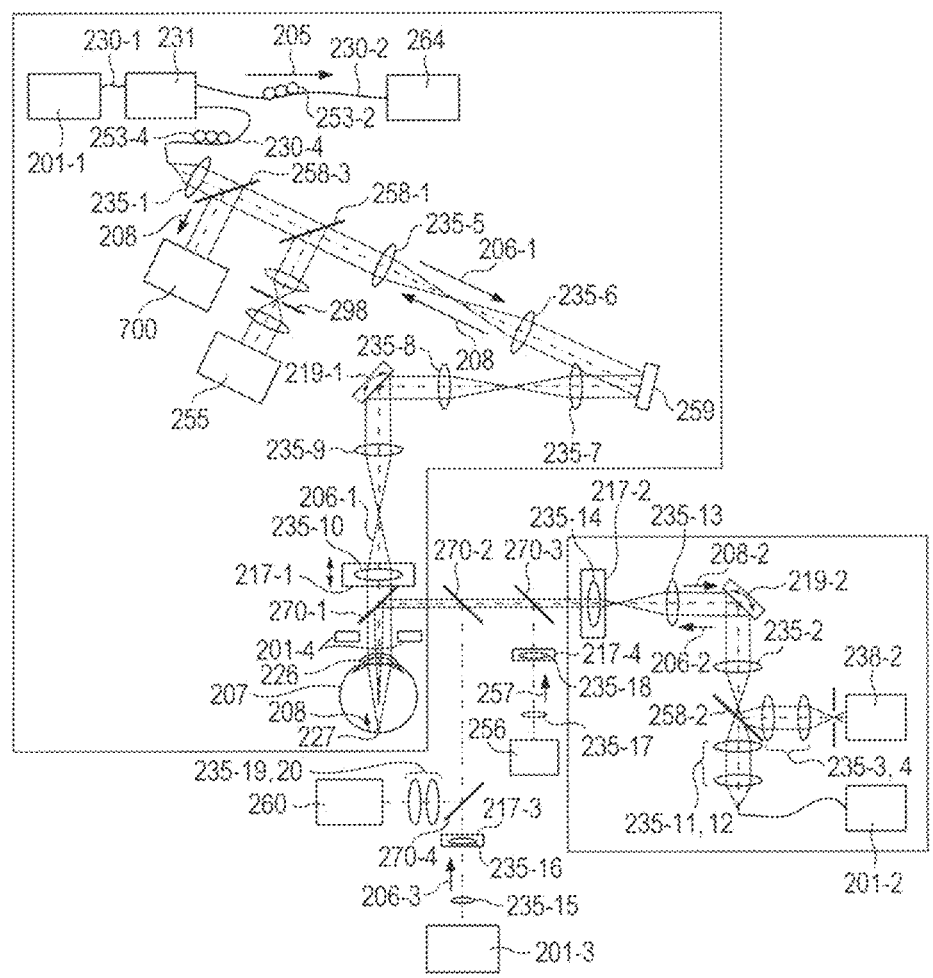
FIG. 2A is a diagram for illustrating a schematic configuration of an optical system of the SLO apparatus according to the embodiment of the present invention.
Figure 2B:
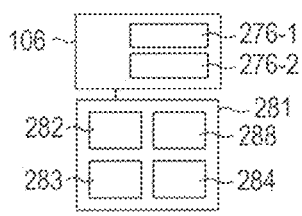
FIG. 2B is a diagram for schematically illustrating a configuration of a control system configured to control the SLO apparatus.

Next, the optical system built in the head unit 102 is specifically described with reference to FIG. 2A and FIG. 2B. As illustrated in FIG. 2A, in the head unit 102, an AO-SLO unit configured to acquire an AO-SLO image, a WF-SLO unit configured to acquire a WF-SLO image, a beacon unit configured to measure a wavefront aberration of the AO-SLO, an anterior ocular segment observation unit configured to acquire an anterior ocular segment observation image, and a fixation target unit that is an optical system configured to prompt the eye to be inspected to fixate. The AO-SLO unit forms an acquiring unit configured to acquire a confocal image and a nonconfocal image of the eye to be inspected in this embodiment.

In this embodiment, the entire optical system is mainly formed of a refracting optical system using lenses. However, it is also possible to form the optical system by using a reflecting optical system using spherical mirrors instead of the lenses.

In addition, a reflective spatial light modulator is used as an aberration compensation device in this embodiment, but it is also possible to use a transmissive spatial light modulator or a deformable mirror.

<Light Source of AO-SLO Unit>

Next, details of a light source 201-1 are described. As the light source 201-1, a super luminescent diode (SLD) serving as a typical low-coherent light source is used. The light acquired by the SLD has a wavelength of 840 nm and a bandwidth of 50 nm. In this case, in order to acquire a planar image having little speckle noise, a low-coherent light source is selected. Further, although the SLD is selected as the light source in this embodiment, any type of light source may be used as long as the light source can emit low-coherent light. For example, an amplified spontaneous emission (ASE) light source may be used.

In view of the measurement of the eye, a suitable wavelength is a near infrared light wavelength. The wavelength affects the lateral resolution of the acquired planar image, and hence the wavelength is desired to be as short as possible. Therefore, in this embodiment, the wavelength is set to 840 nm. Another wavelength may be selected depending on a measurement area of the observation target.

The light emitted from the light source 201-1 is guided to an optical coupler 231 through a single mode fiber 230-1 and split into reference light 205 and measuring light 206-1 in a ratio of 90:10.

<Reference Light Optical Path of AO-SLO Unit>

Next, an optical path of the reference light 205 is described.

The reference light 205 split by the optical coupler 231 enters a light intensity measuring apparatus 264 through an optical fiber 230-2. The light intensity measuring apparatus 264 is used for measuring light intensity of the reference light 205 so as to monitor the light intensity of the measuring light 206-1. Polarization controllers 253-2 are arranged on the optical fiber 230-2 and control the polarization of the reference light 205.

<Measuring Light Optical Path of AO-SLO Unit>

Next, an optical path of the measuring light 206-1 is described.

The measuring light 206-1 split by the optical coupler 231 is guided to a lens 235-1 through a single mode fiber 230-4, and is adjusted to be a collimated light beam having a beam diameter of 4 mm. Polarization controllers 253-4 are arranged on the single mode fiber 230-4 and control polarization of the measuring light 206-1. In an optical path of the measuring light 206-1, a third beam splitter 258-3, a first beam splitter 258-1, a spatial light modulator 259, an AO-SLO XY scanner 219-1, an AO-SLO focusing lens 235-10, and a first dichroic mirror 270-1 are arranged in the stated order from the lens 235-1. Further, a plurality of lenses 235-5 to 235-9 are each arranged between those optical elements appropriately.

The measuring light 206-1 that is formed into a collimated light beam through the lens 235-1 passes through the third beam splitter 258-3, the first beam splitter 258-1, and the lenses 235-5 and 235-6 and enters the spatial light modulator 259.

In this case, the spatial light modulator 259 is controlled by the control unit 106 via a spatial light modulator driver 288 included in a driver unit 281. FIG. 2B is a block diagram for schematically illustrating associated module units built in the control unit 106 and the driver unit 281.

Next, the measuring light 206-1 is modulated by the spatial light modulator 259, passes through lenses 235-7 and 235-8, and enters a mirror of the AO-SLO XY scanner 219-1. For simplification of the illustration, the AO-SLO XY scanner 219-1 is illustrated as a single mirror. However, in an actual case, two mirrors, that is, an X scanner and a Y scanner, are disposed close to each other so as to raster-scan a retina 227 in a direction perpendicular to the optical axis. The center of the measuring light 206-1 is adjusted to align with each center of rotation of the mirrors of the AO-SLO XY scanner 219-1.

The X scanner is a scanner configured to scan the measuring light 206-1 in a direction parallel to the drawing sheet, and a resonance type scanner is used for the X scanner here. The drive frequency is approximately 7.9 kHz. In addition, the Y scanner is a scanner configured to scan the measuring light 206-1 in a direction perpendicular to the drawing sheet, and a galvano scanner is used for the Y scanner here. The drive waveform is a sawtooth wave, the frequency is 32 Hz, and the duty ratio is 84%. The drive frequency of the Y scanner is an important parameter for determining a frame rate of the AO-SLO image acquisition. The AO-SLO XY scanner 219-1 is controlled by the control unit 106 via an optical scanner driver 282 included in the driver unit 281.

The lens 235-9 and the AO-SLO focusing lens 235-10 correspond to an optical system configured to scan the retina 227 in a depth direction and serve to scan the retina 227 with the measuring light 206-1 in a manner of pivoting on the center of a pupil of an eye to be inspected 207. Note that, the beam diameter of the measuring light 206-1 is 4 mm in this embodiment, but the beam diameter may be larger than 4 mm in order to acquire an optical image with higher resolution.

Further, an AO-SLO electric stage 217-1 supporting the AO-SLO focusing lens 235-10 can move in a direction indicated by the arrows so as to move the position of the AO-SLO focusing lens 235-10, to thereby perform focus adjustment. The AO-SLO electric stage 217-1 is controlled by the control unit 106 through an electric stage driver 283 included in the driver unit 281.

The position of the AO-SLO focusing lens 235-10 may be adjusted, to thereby focus the measuring light 206-1 to a predetermined layer of the retina 227 of the eye to be inspected 207 to observe the layer. In addition, it is possible to support the case where the eye to be inspected 207 has ametropia.

The measuring light 206-1 enters the eye to be inspected 207 and is reflected and scattered by the retina 227 so as to be return light 208, which enters a photo-receiving unit 700. The photo-receiving unit 700 has a configuration illustrated in FIG. 3 as described later. The return light 208 having entered the photo-receiving unit 700 is split by a branch portion, and the split light beams reach detectors 704-1 to 704-5, respectively. As the detectors 704-1 to 704-5, for example, an avalanche photo diode (APD) or a photomultiplier tube (PMT) is used, which is a high speed sensor with high sensitivity.

<Photo-Receiving Unit of AO-SLO Unit>

Figure 3:
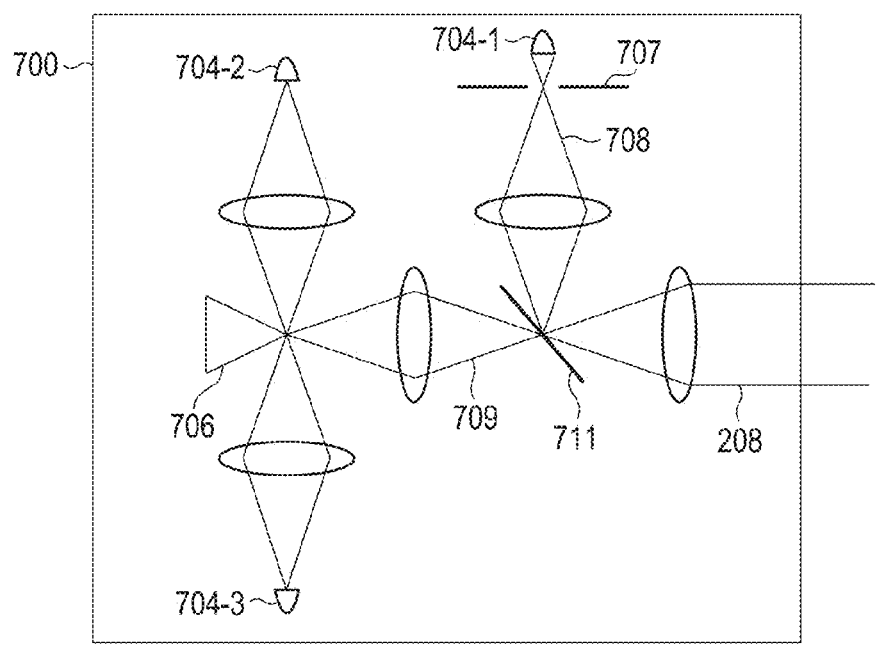
FIG. 3 is a diagram for illustrating a configuration of a photo-receiving unit of the SLO apparatus according to the embodiment of the present invention.
Figure 4:
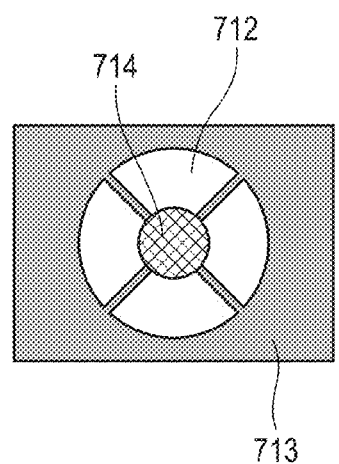
FIG. 4 is a diagram for illustrating a configuration of a second branch portion of the SLO apparatus according to the embodiment of the present invention.

Next, a schematic configuration of the photo-receiving unit 700 is described with reference to FIG. 3. The photo-receiving unit 700 includes the detectors 704-1 to 704-5 (see FIG. 5) described above, a light shielding portion 711, a quadrangular pyramid prism 706, and a plurality of lenses for condensing light. The light shielding portion 711 is described with reference to FIG. 4. The light shielding portion 711 includes four transmission regions 712, a light shielding region 713, and a reflection region 714, and the center of the light shielding portion 711 is arranged so as to be positioned at the center of an optical axis of the return light 208. The light shielding portion 711 has an elliptical pattern that is formed into a circle when viewed from the optical axis direction in a case that the light shielding portion 711 is arranged diagonally with respect to the optical axis of the return light 208.

The return light 208 first enters the light shielding portion 711 arranged on an imaging surface. A part of the incident light to be condensed at a confocal point is split by reflection in the reflection region 714 and enters the detector 704-1 after being condensed. In this case, light 708 split in the light shielding portion 711 enters the detector 704-1 through a shape-variable pinhole 707 arranged on the imaging surface.

Figure 5:
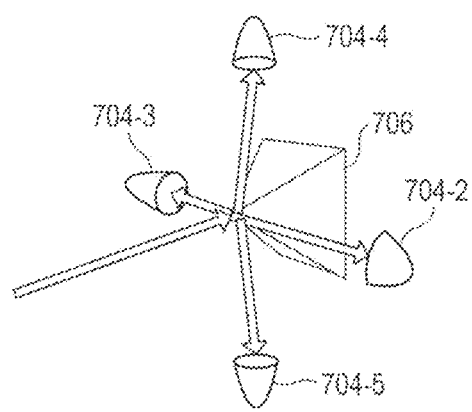
FIG. 5 is a diagram for illustrating a configuration of a first branch portion of the SLO apparatus according to the embodiment of the present invention.

Light 709 having passed through the transmission regions 712 of the light shielding portion 711 is split by the quadrangular pyramid prism 706 arranged on the imaging surface, and the split light beams enter the detectors 704-2, 704-3, 704-4, and 704-5, respectively, as illustrated in FIG. 5. The detectors 704-2 and 704-3 are arranged coaxially with an X-direction during measuring light scanning by the AO-SLO scanner 219-1. Further, the detectors 704-4 and 704-5 are arranged coaxially with a Y-direction during measuring light scanning by the AO-SLO scanner 219-1.

A voltage signal obtained by each detector in accordance with the intensity of the incident light is converted into a digital value by an AD board 276-1 included in the control unit 106 and input to the control unit 106.

<Entire WF-SLO Unit>

Next, the WF-SLO unit is described.

The WF-SLO unit basically has the same configuration as that of the AO-SLO unit. Overlapping description of the same part is omitted.

The WF-SLO unit includes as main components a WF-SLO light source 201-2, a second beam splitter 258-2, a WF-SLO XY scanner 219-2, a WF-SLO focusing lens 235-14, and a WF-SLO detector 238-2. Further, a plurality of lenses 235-2 and 235-11 to 235-14 are each arranged between those optical elements appropriately.

The light output from the WF-SLO light source 201-2 passes through the above-mentioned optical elements and is further guided to the eye to be inspected 207 that is an observation target through dichroic mirrors 270-1 to 270-3 and the like. Similarly to the AO-SLO unit, the WF-SLO light source 201-2 is an SLD. The light to be obtained has a wavelength of 920 nm and a bandwidth of 20 nm.

<Measuring Light Optical Path of WF-SLO Unit>

Next, an optical path of measuring light 206-2 is described.

The measuring light 206-2 emitted from the WF-SLO light source 201-2 is guided to the eye to be inspected 207 that is the observation target through the lenses 235-2 and 235-11 to 235-14, the WF-SLO XY scanner 219-2, the dichroic mirror 270-1, and the like.

The X-scanner that is a component of the WF-SLO XY scanner 219-2 is a scanner configured to scan the measuring light 206-2 in a direction parallel to the drawing sheet, and a resonance type scanner is used for the X scanner here. The drive frequency is approximately 3.9 kHz. In addition, the Y scanner is a scanner configured to scan the measuring light 206-2 in a direction perpendicular to the drawing sheet, and a galvano scanner is used for the Y scanner here. The drive waveform is a sawtooth wave, the frequency is 15 Hz, and the duty ratio is 84%. The drive frequency of the Y scanner is an important parameter for determining a frame rate of the WF-SLO image. The beam diameter of the measuring light 206-2 is 1 mm, but may be larger than 1 mm in order to acquire an optical image with higher resolution.

The measuring light 206-2 enters the eye to be inspected 207 and is reflected or scattered by the retina 227 so as to be return light 208-2, which reaches the second beam splitter 258-2 through the dichroic mirrors 270-1 to 270-3, a lens 235-13, the WF-SLO focusing lens 235-14, the lenses 235-2 to 235-4, the WF-SLO XY scanner 219-2, and the like in an opposite manner to the measuring light 206-2. The return light 208-2 is branched from an optical path of the measuring light 206-2 by the beam splitter 258-2 and reaches the WF-SLO detector 238-2. The WF-SLO focusing lens 235-14 is supported by a WF-SLO electric stage 217-2 and moves in the optical axis direction to enable the focusing of the measuring light 206-2 onto the retina 227.

<Description of Beacon Unit>

Next, the beacon unit configured to measure an aberration generated in the eye to be inspected 207 is described.

Measuring light 206-3 output from a light source 201-3 is guided to the eye to be inspected 207 that is the observation target through a lens 235-15, a beacon focusing lens 235-16, a fourth dichroic mirror 270-4, and the like. In this case, the measuring light 206-3 enters the eye to be inspected 207 under a state of being decentered from the center of the eye to be inspected 207 in order to avoid being reflected from a cornea 226. The beacon focusing lens 235-16 is supported by an electric stage for beacon 217-3 and moves in the optical axis direction to enable the focusing of the measuring light 206-3 onto the retina 227.

A part of return light from the eye to be inspected 207 passes through the optical path of the measuring light 206-1 of the AO-SLO unit in an opposite direction as the return light 208 and reaches the first beam splitter 258-1. The return light 208 branched from the measuring light optical path by the first beam splitter 258-1 enters a wavefront sensor 255 through a pinhole 298. In the wavefront sensor 255, the aberration of the return light 208 generated in the eye to be inspected 207 is measured. In this case, the pinhole 298 is installed for the purpose of shielding unnecessary light other than the return light 208. The wavefront sensor 255 is electrically connected to the control unit 106.

The wavefront sensor 255 is a Shack-Hartmann wavefront sensor, and the measurement range thereof is set to from −10 D to +5 D. The obtained aberration is expressed through use of the Zernike polynomials and indicates the aberration of the eye to be inspected 207. The Zernike polynomials include the following terms: tilt, defocus, astigmatism, coma, trefoil, and the like. Note that, the light source 201-3 has a center wavelength of 760 nm and a wavelength width of 20 nm.

In this case, the lenses 235-5 to 235-10 and the like are arranged so that the cornea 226, the AO-SLO XY scanner 219-1, the wavefront sensor 255, and the spatial light modulator 259 are optically conjugate to each other. Therefore, the wavefront sensor 255 can measure the aberration of the eye to be inspected 207. In addition, the spatial light modulator 259 can compensate the aberration of the eye to be inspected 207 in accordance with an instruction from the control unit 106 based on the information on the aberration sent from the wavefront sensor 255 to the control unit 106.

<Fixation Target Unit>

Figure 6:
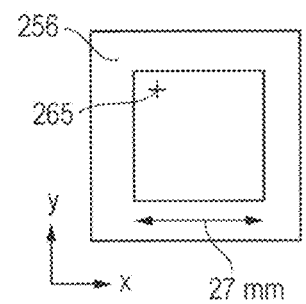
FIG. 6 is a diagram for illustrating a fixation target according to the embodiment of the present invention.

The fixation target 256 is formed of a light-emitting display module and has a display surface (27 mm×27 mm, 128 pixels×128 pixels) on an XY-plane. In this case, a liquid crystal, an organic EL, an LED array, or the like can be used. When the eye to be inspected 207 watches a light flux 257 from the fixation target 256, the eye to be inspected 207 is prompted to fixate or rotate. On the display surface of the fixation target 256, for example, a cross-shaped pattern is displayed so as to blink at any lighting position 265 as illustrated in FIG. 6.

The light flux 257 from the fixation target 256 is guided to the retina 227 through a lens 235-17, a focusing lens 235-18 for a fixation target, and the first to third dichroic mirrors 270-1 to 270-3. Further, the focusing lens 235-18 for a fixation target and the lens 235-17 are arranged so that the display surface of the fixation target 256 and the retina 227 are optically conjugate to each other. The focusing lens 235-18 for a fixation target is supported by an electric stage 217-4 for a fixation target and moves in the optical axis direction to enable a clear image to be presented to the eye to be inspected 207. Further, the fixation target 256 is controlled by the control unit 106 via a fixation target driver 284 included in the driver unit 281.

<Anterior Ocular Segment Observation Unit>

Next, the anterior ocular segment observation unit is described.

Light output from an anterior ocular segment illumination light source 201-4 illuminates the eye to be inspected 207. The light reflected from the eye to be inspected 207 enters a CCD camera 260 through the first dichroic mirror 270-1, the second dichroic mirror 270-2, the fourth dichroic mirror 270-4, and lenses 235-19 and 235-20. The anterior ocular segment illumination light source 201-4 is an LED having a center wavelength of 740 nm.

<Focus, Shutter, and Astigmatism Correction>

As described above, the optical system built in the head unit 102 includes the AO-SLO unit, the WF-SLO unit, the beacon unit, the fixation target unit, and the anterior ocular segment observation unit. Of those, the AO-SLO unit, the WF-SLO unit, the beacon unit, and the fixation target unit have the electric stages 217-1 to 217-4 for focusing described above, respectively and individually, and through the coordinated movement of the four electric stages 217-1 to 217-4, the focus of the focusing lens supported by each of the electric stages 217-1 to 217-4 is adjusted. Note that, in the case where a focus position is intended to be adjusted individually, the electric stage can also be moved individually.

Further, the AO-SLO unit, the WF-SLO unit, and the beacon unit each include a shutter (not shown), and whether or not the measuring light is caused to enter the eye to be inspected 207 can be controlled by opening or closing the shutter. Note that, the shutter is used here, but whether or not the measuring light is caused to enter the eye to be inspected 207 can also be controlled by directly turning on/off the light sources 201-1 to 201-3. Similarly, the anterior ocular segment observation unit and the fixation target unit can also be controlled by turning on/off the light source 201-4 and the fixation target 256.

Further, the AO-SLO focusing lens 235-10 can be replaced, and a spherical lens or a cylindrical lens may be used in accordance with the aberration (ametropia) of the eye to be inspected 207. Further, the number of the lenses is not limited to one, and a plurality of lenses may be combined and installed.

<Wavelength>

Figure 7:
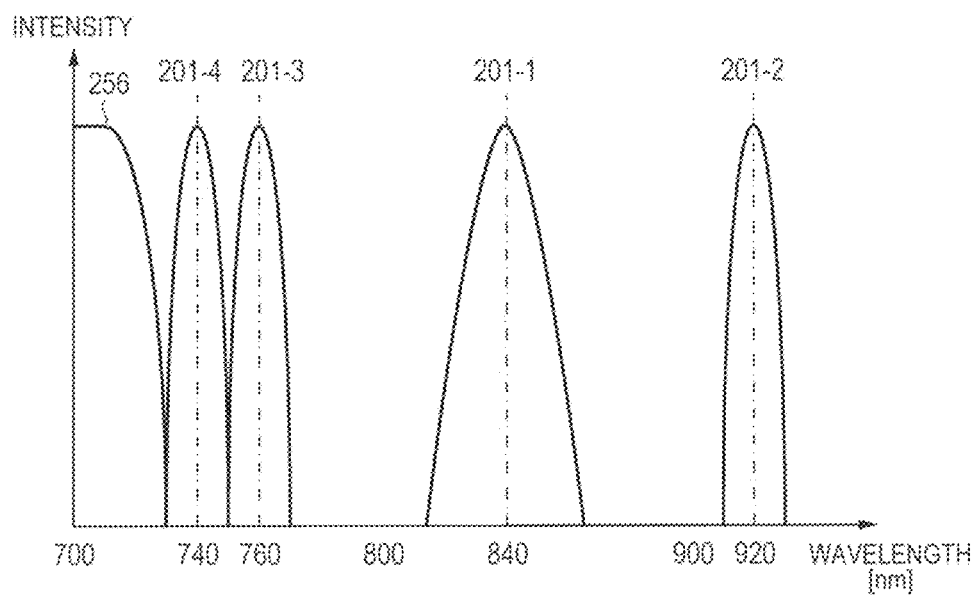
FIG. 7 is a graph for showing a wavelength distribution of each light beam guided to an eye to be inspected, such as measuring light, of the SLO apparatus according to the embodiment of the present invention.

The wavelength distribution of light beams emitted from the light sources used in the AO-SLO unit, the WF-SLO unit, the beacon unit, the fixation target unit, and the anterior ocular segment observation unit is shown in FIG. 7. In order to separate the light beams by the dichroic mirrors 270-1 to 270-4, the light beams are set to have different wavelength bands. Note that, the difference in wavelength of the respective light beams is shown in FIG. 7, and the intensity and spectrum shape are not defined therein.

<Imaging>

Next, a method of forming an acquired image is described.

The light that has entered the detectors 704-1 to 704-5 is subjected to photoelectric conversion in each of the detectors 704-1 to 704-5 and is converted into a digital value by the AD board 276-1 included in the control unit 106. In the control unit 106, the digital value is further subjected to data processing synchronized with the operation and drive frequency of the AO-SLO XY scanner 219-1, to thereby form an AO-SLO image.

An AO-SLO image formed based on the light having entered the detector 704-1, that is, the light reflected from the reflection region 714 in the light shielding portion 711 corresponding to a pinhole, is a confocal image. Meanwhile, an AO-SLO image formed based on the light having entered the detectors 704-2 to 704-5, that is, the scattering light having passed through the transmission regions 712 on the periphery of the reflection region 714 in the light shielding portion 711 corresponding to the pinhole, is a nonconfocal image.

Digital values obtained from each light beam at certain time when the light beams enter the detectors 704-2, 704-3, 704-4, and 704-5 are respectively defined as Ia, Ib, Ic, and Id. Then, differential values I' and I" in the X-direction and the Y-direction can be determined based on the following expressions.

$$I'=(Ia-Ib)/(Ia+Ib)$$

$$I''=(Ic-Id)/(Ic+Id)$$

Through use of an image generated with the differential values I' and I" in the X-direction and the Y-direction, an image with an outline emphasized can be acquired. Further, as the configuration of the photo-receiving unit, the configuration is described in which the number of the detectors is set to four to acquire the digital values Ia, Ib, Ic, and Id. However, another configuration may be considered. For example, there may be adopted a configuration in which two detectors are arranged so as to be line-symmetric with respect to a branched point of the quadrangular pyramid prism, and a drive unit configured to rotate around the branched point is provided with respect to the branched direction of the quadrangular pyramid prism and the two detectors. In the case of this configuration, when the quadrangular pyramid prism and the detectors are rotated around the optical axis of the light 709, the information on the differential value I' and the rotation angle can be acquired.

Similarly, in the WF-SLO unit, a voltage signal obtained in the WF-SLO detector 238-2 is converted into a digital value by the AD board 276-2 included in the control unit 106, to thereby form a WF-SLO image.

<Imaging Procedure>

Next, an imaging procedure in the AO-SLO apparatus 101 according to this embodiment is described with reference to FIG. 8, FIG. 9, and FIGS. 10A to 10D.

Figure 8:
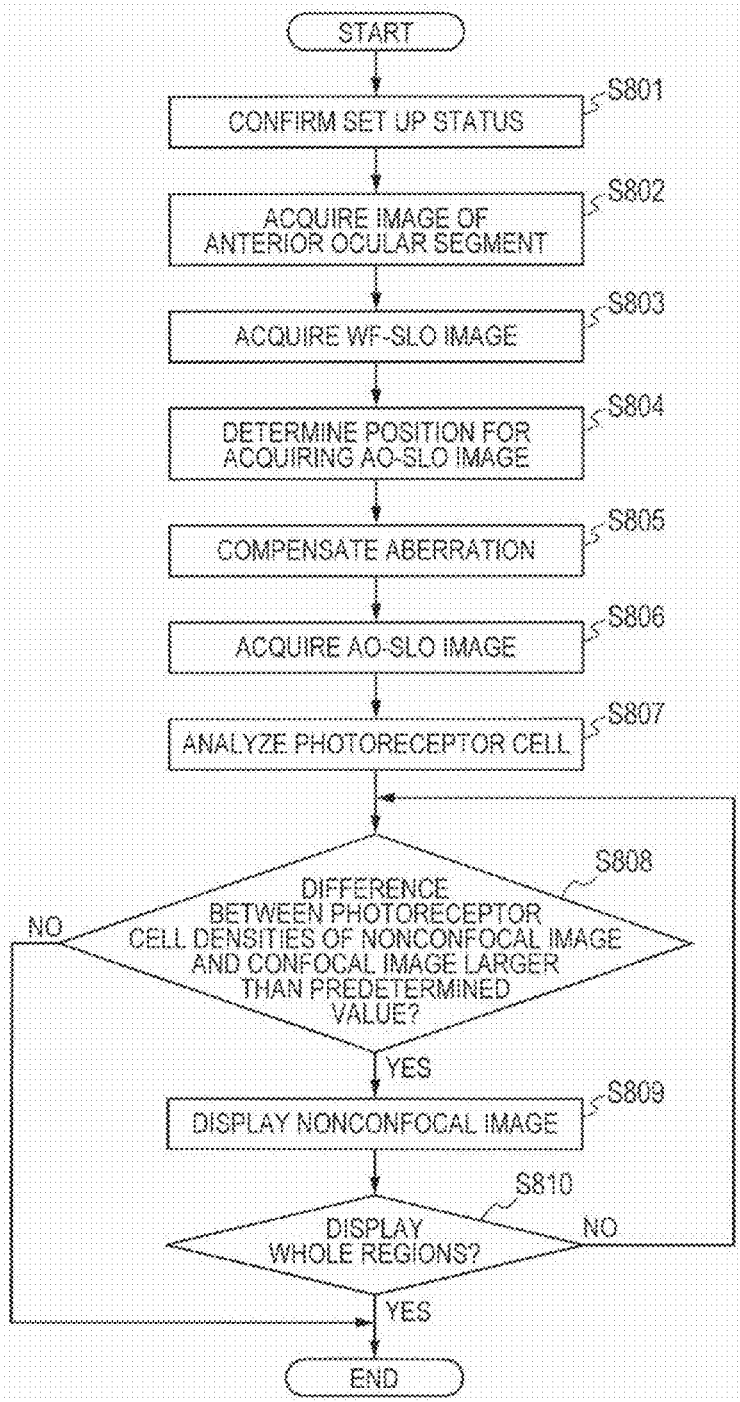
FIG. 8 is a flowchart for illustrating an imaging procedure of the SLO apparatus according to the embodiment of the present invention.

FIG. 8 is a flowchart for illustrating the imaging procedure. Each step is described below in detail.

(Step S801) The AO-SLO apparatus 101 is started up, and the setup status of the AO-SLO apparatus 101 is confirmed.

Figure 9:
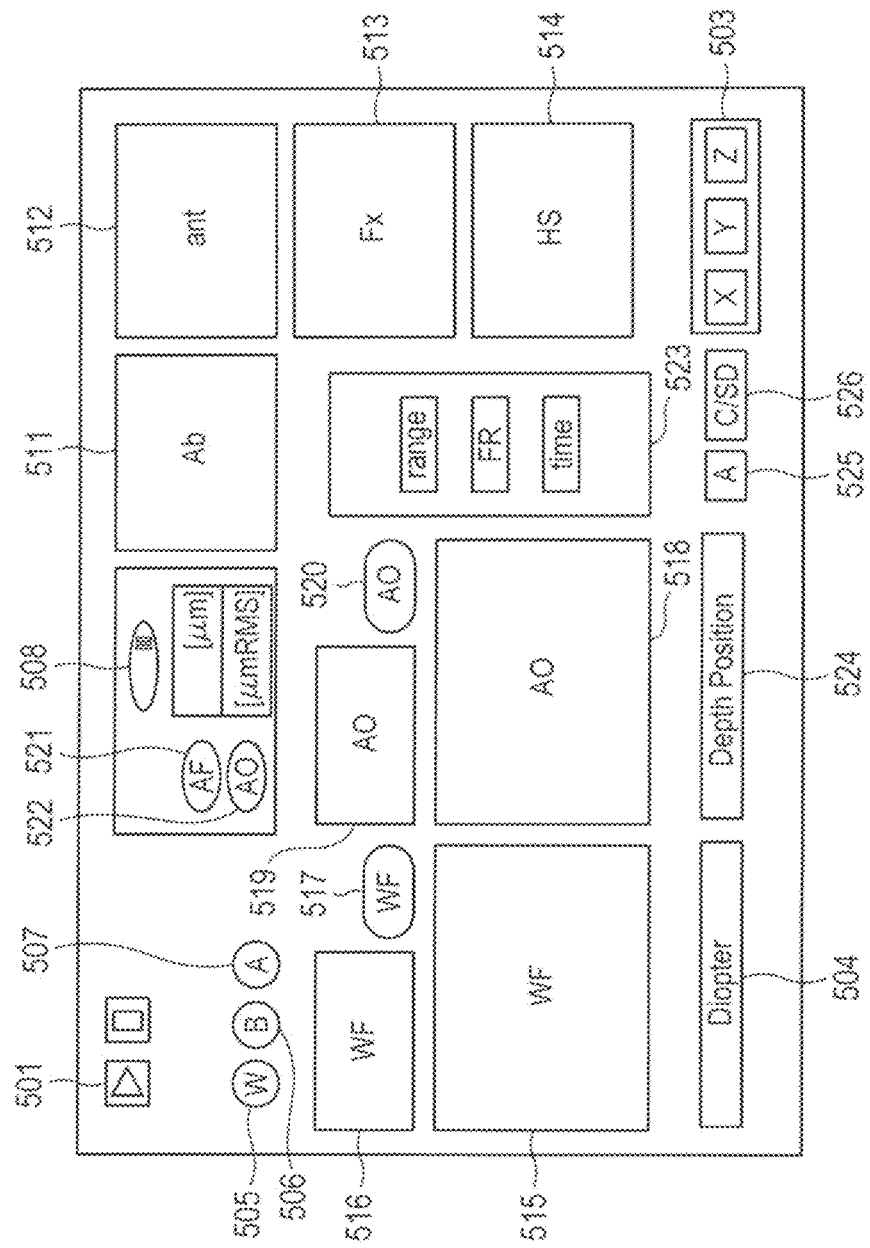
FIG. 9 is a diagram for illustrating a configuration of a screen of an image browser of the SLO apparatus according to the embodiment of the present invention.

An examiner turns on the power sources of the control unit 106 and the AO-SLO apparatus 101. Then, when control software for measurement is activated, a control software screen illustrated in FIG. 9 is displayed on the display unit 105. At this time, a subject is urged to put a face on the face receiving unit 104.

(Step S802) An image of an anterior ocular segment is acquired.

When an execution button 501 on the control software screen is pressed, an image of an anterior ocular segment is displayed on an anterior ocular segment monitor 512. In the case where the center of a pupil is not correctly displayed at the center of the monitor, the head unit 102 is first moved to a substantially correct position through use of the joystick 107. In the case where further adjustment is required, an electric stage button 503 on the control software screen is pressed to slightly move the chin holder drive unit 109.

(Step S803) A WF-SLO image is acquired.

In this step, the scanning width of the WF-SLO XY scanner 219-2 is adjusted, and a fundus of the eye of the subject is imaged with a size of 8 mm×6 mm. In the case where the image of the anterior ocular segment is displayed in a substantially correct state, a WF-SLO image is displayed on a WF-SLO monitor 515. The fixation target 256 is set at a center position with a fixation target position monitor 513 to guide a line of sight of the eye to be inspected 207 to the center.

Next, the examiner adjusts a focus adjustment button 504 so as to increase WF-SLO intensity while watching a WF-SLO intensity monitor 516. On the WF-SLO intensity monitor 516, signal intensity detected by the WF-SLO unit is displayed in a time series, with the horizontal axis being time and the vertical axis being signal intensity. Then, through adjustment of the focus adjustment button 504, the positions of the focusing lenses 235-10, 235-14, 235-16, and 235-18 are adjusted concurrently.

In the case where the WF-SLO image is displayed clearly, a WF-SLO imaging button 505 is pressed to acquire the WF-SLO image. In the case where there is no problem in the acquired WF-SLO image, a WF-SLO recording button 517 is pressed to save WF-SLO data on the WF-SLO image.

(Step S804) A position for acquiring an AO-SLO image is determined.

The displayed WF-SLO image is confirmed, and a position at which an AO-SLO image is intended to be acquired is determined through use of a method described later. Next, the line of sight of the eye to be inspected 207 is guided so that the position for acquiring an AO-SLO image is placed at the center of the WF-SLO monitor 515.

There are two methods of determining the position for acquiring an AO-SLO image. One of the methods is a method involving designating the position of the fixation target 256 in the fixation target position monitor 513, and the other is a method involving clicking on an intended position on the WF-SLO monitor 515. Pixels on the WF-SLO monitor 515 are associated with the position of the fixation target 256 so that the position of the fixation target 256 can move automatically to guide the line of sight to an intended position.

After it is confirmed that the position at which an AO-SLO image is intended to be acquired has moved to the center on the WF-SLO monitor 515, the flow shifts to the subsequent step.

(Step S805) An aberration is compensated.

When an aberration measurement button 506 is pressed, the measuring light 206-2 serving as the WF-SLO measuring light is blocked, and the shutter (not shown) of the beacon unit is opened, with the result that the measuring light 206-3 serving as beacon light is radiated to the eye to be inspected 207. A Hartman image detected by the wavefront sensor 255 is displayed on a wavefront sensor monitor 514. An aberration calculated based on the Hartman image is displayed on an aberration compensation monitor 511. The aberration is displayed so as to be separated into a defocus component (unit: μm) and the entire aberration amount (unit: μmRMS). In this case, the positions of the AO-SLO focusing lens 235-10 for the AO-SLO measuring light and the beacon focusing lens 235-16 for the beacon light are adjusted in Step S803, and hence aberration measurement is ready to be performed in Step S805. Specifically, the return light 208 with respect to the measuring light 206-3 passes through the pinhole 298 without being blocked and is in a state of reaching the wavefront sensor 255.

In this case, when an automatic focus button 521 is pressed, the positions of the lenses 235-10, 235-14, 235-16, and 235-18 are automatically adjusted so that the value of defocus decreases.

Next, when an aberration compensation button 522 is pressed, the spatial light modulator 259 is automatically adjusted so that the aberration amount decreases, and the value of the aberration amount is displayed in real time. In this case, when the value of the aberration amount reaches a threshold value (0.03 μmRMS) or less determined in advance, an AO-SLO measurement button 507 is automatically pressed, and the flow shifts to the subsequent step. The threshold value of the aberration amount can be set arbitrarily. Further, in the case where the value of the aberration amount does not reach the threshold value or less, an aberration compensation temporary stop button 508 is pressed to stop the aberration compensation. After that, the AO-SLO measurement button 507 is pressed to cause the flow to shift to the subsequent step.

In this case, the scanning width of the WF-SLO XY scanner 219-2 is adjusted, and the fundus of the eye of the subject is imaged with a size of 200 μm×200 μm and a resolution of 400 pixels×400 pixels.

(Step S806) An AO-SLO image is acquired.

When the AO-SLO measurement button 507 is pressed, the measuring light 206-3 serving as the beacon light is blocked, and the shutter of the AO-SLO measuring light 206-1 is opened, with the result that the measuring light 206-1 is radiated to the eye to be inspected 207. An AO-SLO image having the aberration compensated is displayed on an AO-SLO monitor 518. The AO-SLO image thus displayed is an AO-SLO confocal image described later. Further, similarly to the WF-SLO intensity monitor 516, signal intensity detected by the AO-SLO unit is displayed in a time series on an AO-SLO intensity monitor 519.

In the case where the signal intensity is insufficient, the examiner adjusts focus and a chin holding position while watching the AO-SLO intensity monitor 519 so that the signal intensity increases.

Further, an imaging field angle, a frame rate, and an imaging time can be designated by imaging condition setting buttons 523.

Further, through adjustment of a depth adjustment button 524, the AO-SLO focusing lens 235-10 can be moved to adjust the imaging range in the depth direction of the eye to be inspected 207. Specifically, an image of an intended layer, such as a photoreceptor cell layer, a nerve fiber layer, or a pigment epithelial layer, can be acquired.

In the case where the AO-SLO image is clearly displayed, an AO-SLO recording button 520 is pressed to save AO-SLO data. Then, the measuring light 206-1 is blocked. Here, in the control unit 106, an AO-SLO confocal image is formed based on the light having entered the detector 704-1 and an AO-SLO nonconfocal image is formed based on the light having entered the detectors 704-2 to 704-5. In this case, the AO-SLO nonconfocal image is formed through use of the differential value I' in the X-direction described in the section of imaging. The formed nonconfocal image is not displayed on the control software screen illustrated in FIG. 9.

Figure 10:
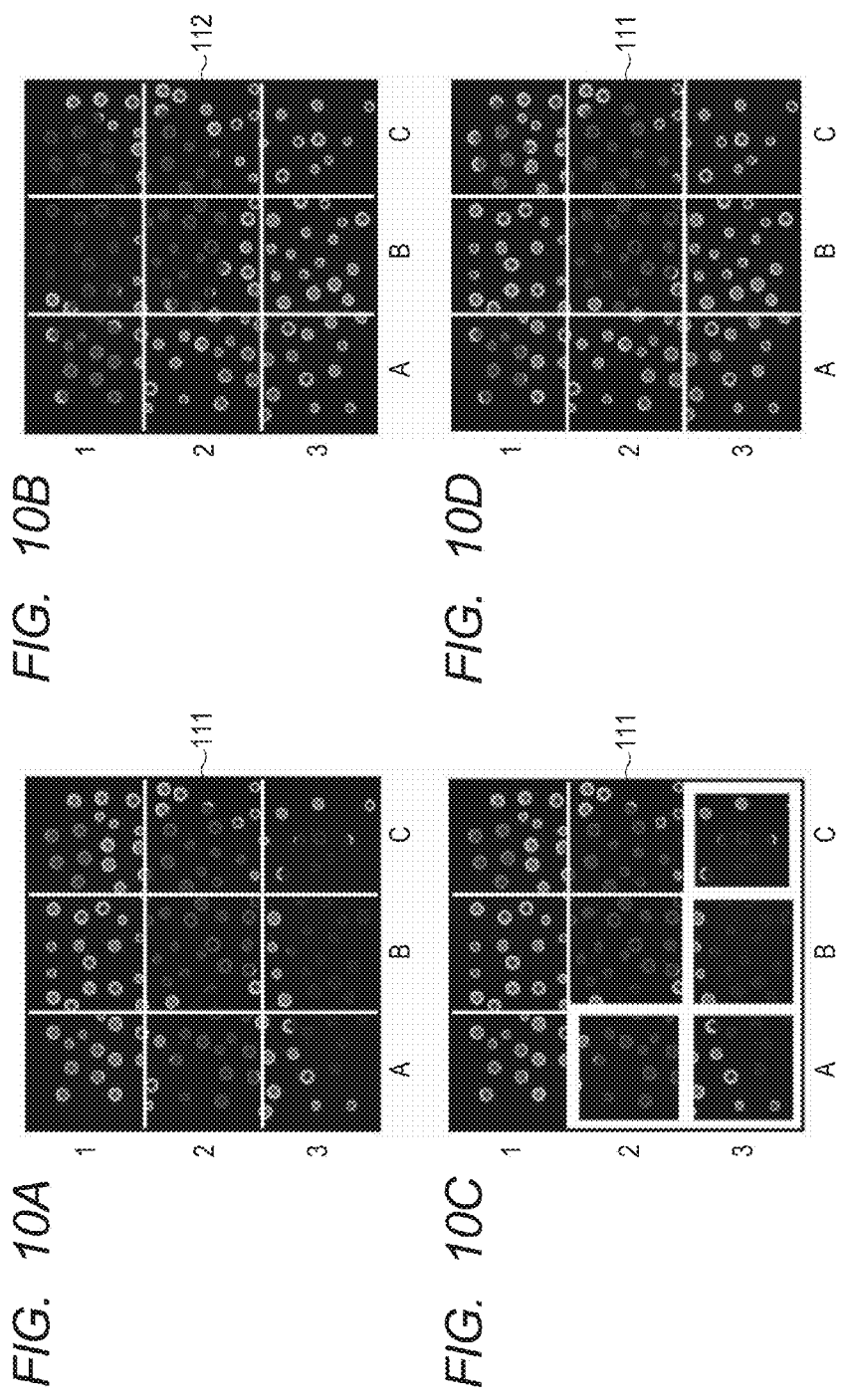
FIGS. 10A, 10B, 10C and 10D are each a diagram for illustrating an AO-SLO image displayed on an AO-SLO monitor according to a first embodiment of the present invention.

FIG. 10A to FIG. 10D are each a diagram for illustrating the formed AO-SLO image. FIG. 10A is an illustration of an AO-SLO confocal image 111, and FIG. 10B is an illustration of an AO-SLO nonconfocal image 112. The AO-SLO confocal image 111 and the AO-SLO nonconfocal image 112 are equally divided, for example, into A to C and 1 to 3 in the X-direction and the Y-direction, respectively, and each include nine regions.

(Step S807) The state of photoreceptor cells in the AO-SLO image is analyzed.

Next, when a photoreceptor cell analysis button 525 is pressed, the photoreceptor cells are detected based on known image processing (such as the method described in U.S. Patent Application Publication No. 2014/0185889) with respect to the AO-SLO confocal image 111 and the AO-SLO nonconfocal image 112. The detection of the photoreceptor cells and the comparison of photoreceptor cell densities in the subsequent Step S808 are performed by a module serving as an analysis unit configured to analyze the confocal image and the nonconfocal image arranged on the AD board 276-1.

Note that, the analysis unit also includes a module serving as an image dividing unit configured to divide an image into a plurality of regions during execution of analysis. Further, the photoreceptor cell density in this embodiment is one of a plurality of predetermined inspection or evaluation items considered during inspection of a fundus of the eye, and the calculation of the photoreceptor cell density corresponds to the calculation of the evaluation value thereof. The calculation of the photoreceptor cell density is performed by an evaluation value calculating unit included in the analysis unit.

(Step S808) Photoreceptor cell densities are compared with each other.

Next, the densities of the detected photoreceptor cells are compared with each other for each region obtained by dividing the AO-SLO confocal image 111 and the AO-SLO nonconfocal image 112 into nine. At this time, a region X is detected in which the photoreceptor cell density detected in the AO-SLO nonconfocal image 112 is larger by a predetermined value or more than the photoreceptor cell density detected in the AO-SLO confocal image 111. In this case, regions 2-A, 3-A, 3-B, and 3-C were detected as the region X. The detected region X is displayed with a frame border surrounding the region X being thick as illustrated in FIG. 10C so that the examiner is notified of the fact that the photoreceptor cells are observed more easily in the AO-SLO nonconfocal image 112 than in the AO-SLO confocal image 111 displayed on the AO-SLO monitor 518. This notification is performed via various notification forms, such as insertion of letters and insertion of a frame, by a display control unit configured to change the display form of an image to be displayed on the display unit 105 in accordance with the analysis results. The display control unit is formed of a module serving as a display control unit in the AD board 276-1 included in the control unit 106.

(Step S809) An AO-SLO nonconfocal image is displayed.

Next, a confocal image/nonconfocal image switch button 526 is pressed to display the AO-SLO nonconfocal image 112 in the regions 2-A, 3-A, 3-B, and 3-C of the AO-SLO monitor 518, and photoreceptor cells are observed. The confocal image/nonconfocal image switch button 526 switches between a confocal image and a nonconfocal image by being pressed (FIG. 10C and FIG. 10D are switched), and hence the examiner can display an intended AO-SLO image. Note that, an example in which the entire region X is switched is described above. However, a configuration in which the region X is switched for one region may be adopted, and further, a nonconfocal image may be displayed in the case where an instruction is given by a pointing device, such as a mouse.

Specifically, an image to be displayed on the AO-SLO monitor 518 is changed in accordance the comparison results of the evaluation values described above. The change in the display form in accordance with the comparison results that are analysis results is performed by the module serving as the display control unit described above.

(Step S810) It is confirmed whether or not the whole regions have been considered for switching.

Whether or not the displayed whole divided regions have been considered regarding the necessity or unnecessity of switching a confocal image to a nonconfocal image is displayed. When the whole regions have been considered, a series of operations is finally finished. When the whole regions have not been considered, the flow shifts to Step S808 to consider whether or not a region that has not been considered needs be switched.

Through the execution of the above-mentioned steps, an AO-SLO image of a fundus of the eye suitable for diagnosis can be acquired easily and rapidly, and an image intended by the examiner can be provided. Note that, in the above-mentioned embodiment, the display unit 105 is intended to display a confocal image, but it is sufficient that the display unit 105 can display at least one of a confocal image and a nonconfocal image. One of a confocal image and a nonconfocal image may be displayed and replaced by another image in accordance with the analysis results.

Second Embodiment

In the first embodiment, the method involving successively displaying the AO-SLO confocal image 111 and the AO-SLO nonconfocal image 112 on the AO-SLO monitor 518 by pressing the confocal image/nonconfocal image switch button 526 is described. However, in each corresponding region in the divided regions, only the region X, in which the photoreceptor cell density of the AO-SLO nonconfocal image 112 is larger by a predetermined value or more than that of the AO-SLO confocal image 111, may be displayed by being replaced by the AO-SLO nonconfocal image 112. FIG. 10D is a diagram in which the AO-SLO nonconfocal image 112 is fitted into the regions 2-A, 3-A, 3-B, and 3-C detected as the region X with respect to the AO-SLO confocal image 111.

Third Embodiment

In the first embodiment, the method involving comparing the photoreceptor cell density of the AO-SLO confocal image 111 with the photoreceptor cell density of the AO-SLO nonconfocal image 112 for each of the nine divided regions and displaying the comparison results is described. In a third embodiment of the present invention, a method involving dividing an AO-SLO image into a larger number of regions, comparing the photoreceptor cell density of the AO-SLO confocal image 111 with the photoreceptor cell density of the AO-SLO nonconfocal image 112, and displaying the comparison results is described.

In the third embodiment, in Step S808 of the first embodiment, the photoreceptor cell density of the AO-SLO confocal image 111 and the photoreceptor cell density of the AO-SLO nonconfocal image 112 are compared with each other for each minute region, such as a region of 15 µm×15 µm. A ratio T between a photoreceptor cell density C of the AO-SLO confocal image 111 and a photoreceptor cell density S of the AO-SLO nonconfocal image 112 is calculated so that the comparison results can be divided into, for example, four stages. In this case, the ratio T of the photoreceptor cell density S of the AO-SLO nonconfocal image with respect to the photoreceptor cell density C of the AO-SLO confocal image is obtained. Further, the AO-SLO nonconfocal image 111 is divided based on four kinds of ranks in accordance with the following calculation results of the ratio T.

A: $3 \leq T$
B: $2 \leq T < 3$
C: $1 \leq T < 2$
D: $T < 1$

Figure 11:
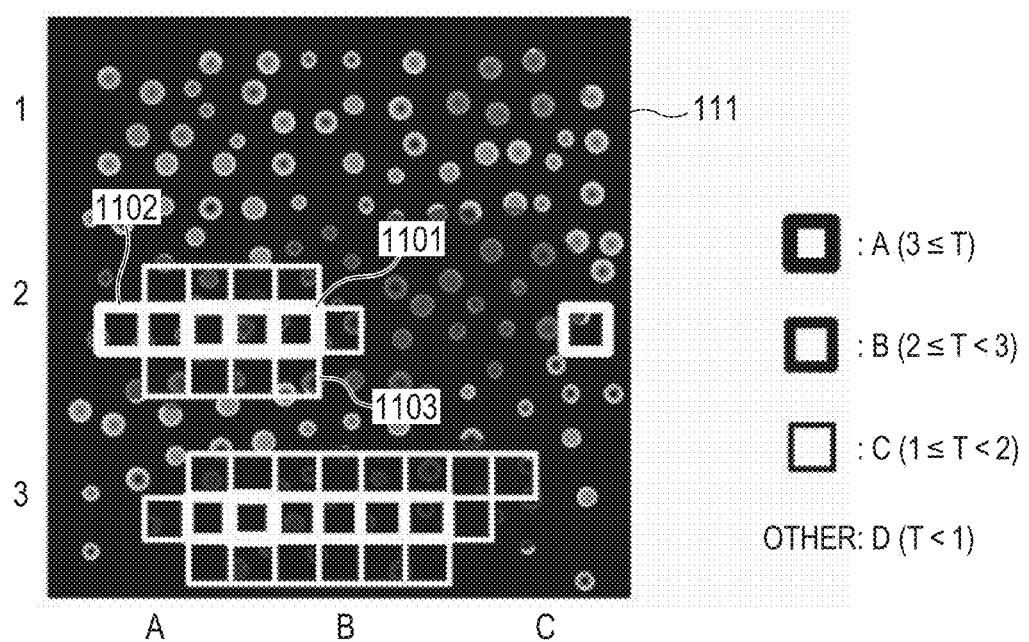
FIG. 11 is a diagram for illustrating an AO-SLO image displayed on an AO-SLO monitor according to a third embodiment of the present invention.

FIG. 11 is an illustration of an image displayed so that a region in accordance with the ratio T calculated for the AO-SLO confocal image 111 is superimposed on the AO-SLO confocal image 111. In FIG. 11, the state of the AO-SLO confocal image 111 divided into four regions including a region A (1101), a region B (1102), a region C (1103), and the other region D is illustrated. The examiner can grasp a region having a large ratio T of the photoreceptor cell density S of the AO-SLO nonconfocal image 112 with respect to the photoreceptor cell density C of the AO-SLO confocal image 111 by observing the AO-SLO confocal image 111 illustrated in FIG. 11.

With this, the examiner can observe photoreceptor cells by pressing the confocal image/nonconfocal image switch button 526 to display the AO-SLO nonconfocal image 102 on the AO-SLO monitor 518, as necessary.

Further, in order to display the regions A to C, for example, a method involving using a color frame or displaying a semitransparent image by changing the transmittance in accordance with the value of the ratio T of the photoreceptor cell densities may be used instead of displaying the regions A to C through the thick frame border as illustrated in FIG. 11. That is, in this embodiment, corresponding positions of the AO-SLO confocal image 111 and the AO-SLO nonconfocal image 112 or regions are ranked in accordance with a difference in evaluation value between the positions, and the mode for replacing the images is changed in accordance with the ranking.

Further, in the second embodiment, the method involving calculating the ratio T of the photoreceptor cell densities for each minute region is described. However, a method involving calculating the ratio T of the photoreceptor cell densities for adjacent minute regions, such as 3×3 regions, is also effective.

Other Embodiments

In the above-mentioned embodiments, the cases of obtaining image information on photoreceptor cells are described, but the image information targeted by the present invention is not limited thereto. For example, the above-mentioned analysis methods can also be applied to various structures capable of being analyzed as various images, which can be collected from a fundus of the eye, such as a retinal vessel, through images.

Further, the present invention is not limited to the above-mentioned embodiments, but can be embodied with various changes and modifications without departing from the spirit of the present invention. For instance, although the object to be inspected is an eye in the above-mentioned embodiments, the present invention can be applied to an object to be measured other than an eye, such as skin or an organ. In this case, the present invention includes an aspect as medical devices, such as an endoscope, other than ophthalmic apparatus. Thus, it is desired that the present invention be grasped as an imaging apparatus exemplified as an apparatus for ophthalmic diagnosis and treatment, and an eye to be inspected be grasped as one aspect of an object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-028532, filed Feb. 17, 2015, which is hereby incorporated by reference wherein in its entirety.

What is claimed is:

1. An imaging apparatus comprising:
an acquiring unit configured to acquire a confocal image and a nonconfocal image of an eye to be inspected;
a display unit configured to display at least one of the acquired confocal image and the acquired nonconfocal image;
an analysis unit configured to analyze the acquired confocal image and the acquired nonconfocal image; and
a display control unit configured to change a display form displayed on the display unit in accordance with an analysis result obtained by the analysis unit,
wherein the analysis unit comprises an evaluation value calculating unit configured to calculate evaluation values in the acquired confocal image and the acquired nonconfocal image regarding a predetermined evaluation item, and wherein the display control unit is configured to change the display form in accordance with a comparison result of the corresponding evaluation values in the acquired confocal image and the acquired nonconfocal image.

2. An imaging apparatus according to claim 1,
wherein the analysis unit comprises an image dividing unit configured to divide the acquired confocal image and the acquired nonconfocal image into a plurality of regions, and
wherein the analysis unit is configured to analyze the acquired confocal image and the acquired nonconfocal image with respect to each of the plurality of divided regions of the acquired confocal image and the acquired nonconfocal image.

3. An imaging apparatus according to claim 1, wherein the display control unit is configured to cause the display unit to display a notification form of notifying an examiner of the analysis result.

4. An imaging apparatus according to claim 1, wherein the display control unit is configured to, when the evaluation values are compared with each other, replace the confocal image by the nonconfocal image in a case where the evaluation value of the nonconfocal image is larger than the evaluation value of the confocal image by a predetermined value or more.

5. An imaging apparatus according to claim 1,
wherein the analysis unit is configured to, when the evaluation values are compared with each other, perform ranking in accordance with a difference between the evaluation value of the nonconfocal image and the evaluation value of the confocal image, and
wherein the display control unit is configured to change a mode of replacing the confocal image by the nonconfocal image in accordance with the ranking.

6. An imaging apparatus according to claim 1, wherein the analysis unit is configured to analyze a state of a photoreceptor cell of the eye to be inspected.

7. An imaging apparatus according to claim 1,
wherein the analysis unit is configured to, when the evaluation values are compared with each other, detect one or more regions that has the evaluation value of the confocal image smaller than the evaluation value of the nonconfocal image in accordance with a difference between the evaluation value of the nonconfocal image and the evaluation value of the confocal image, and wherein the display control unit is configured to change a mode of replacing the confocal image in the one or more regions by the nonconfocal image.

8. A control method for an imaging apparatus, the control method comprising:
acquiring a confocal image and a nonconfocal image of an eye to be inspected;
displaying at least one of the acquired confocal image and the acquired nonconfocal image on a display unit;
analyzing the acquired confocal image and the acquired nonconfocal image; and
changing a display form displayed on the display unit in accordance with an analysis result obtained in the analyzing the acquired confocal image and the acquired nonconfocal image,
wherein in the analyzing step, evaluation values are calculated in the acquired confocal image and the acquired nonconfocal image regarding a predetermined evaluation item, and
wherein in the changing step, the display form is changed in accordance with a comparison result of the corresponding evaluation values in the acquired confocal image and the acquired nonconfocal image.

9. A non-transitory tangible medium having recorded thereon a program for causing a computer to perform steps of a control method for an imaging apparatus, the control method comprising:
acquiring a confocal image and a nonconfocal image of an eye to be inspected;
displaying at least one of the acquired confocal image and the acquired nonconfocal image on a display unit;
analyzing the acquired confocal image and the acquired nonconfocal image; and
changing a display form displayed on the display unit in accordance with an analysis result obtained in the analyzing the acquired confocal image and the acquired nonconfocal image,
wherein in the analyzing step, evaluation values are calculated in the acquired confocal image and the acquired nonconfocal image regarding a predetermined evaluation item, and
wherein in the changing step, the display form is changed in accordance with a comparison result of the corresponding evaluation values in the acquired confocal image and the acquired nonconfocal image.

* * * * *